US009217722B2

(12) United States Patent
Mirsky et al.

(10) Patent No.: US 9,217,722 B2
(45) Date of Patent: Dec. 22, 2015

(54) MULTI-ELECTRODE CHEMIRESISTOR

(75) Inventors: Vladimir Mirsky, Dresden (DE); Ulrich Lange, Stuttgart (DE)

(73) Assignee: Brandenburgische Technische Universitaet Cottbus- Senftenberg, Senftenberg (DE)

( * ) Notice: Subject to any disclaimer, the term of this patent is extended or adjusted under 35 U.S.C. 154(b) by 712 days.

(21) Appl. No.: 13/383,568

(22) PCT Filed: Jul. 13, 2010

(86) PCT No.: PCT/EP2010/004406
§ 371 (c)(1),
(2), (4) Date: Apr. 2, 2012

(87) PCT Pub. No.: WO2011/006677
PCT Pub. Date: Jan. 20, 2011

(65) Prior Publication Data
US 2012/0186987 A1    Jul. 26, 2012

(30) Foreign Application Priority Data
Jul. 13, 2009  (EP) ................................ 09075311

(51) Int. Cl.
*G01N 27/26* (2006.01)
*G01N 27/12* (2006.01)

(52) U.S. Cl.
CPC .................... *G01N 27/126* (2013.01)

(58) Field of Classification Search
CPC .................................................. G01N 27/126
USPC ........................................ 205/334; 204/402
See application file for complete search history.

(56) References Cited

U.S. PATENT DOCUMENTS

2009/0294277 A1* 12/2009 Thomas et al. ............ 204/192.1
2011/0266161 A1* 11/2011 Tao et al. ...................... 205/792

FOREIGN PATENT DOCUMENTS

WO         2008/033419 A2    3/2008

OTHER PUBLICATIONS

Chao et al., J.Am.Chem.Soc., 1997, 109, 6627-6631.*
Ofer D et al: "Potential dependence of 1,5, the conductivity of highly oxidized 7-11, polythiophenes, polypyrroles, and 13-16, polyaniline: finite windows of high 21,24,25 conductivity" in: Journal of the American Chemical Society USA, vol. 112, No. 22, 1990-10-24, pp. 7869-7879.
Ikariyama Yoshihito et al: "Polypyrrole 17-20 Electrode as a Detector for Electroinactive Anions by Flow Injection Analysis" in: Analytical Chemistry, American Chemical Society, US , vol. 58, No. 8, Jul. 1, 1986, pp. 1803-1806.

(Continued)

*Primary Examiner* — Gurpreet Kaur
(74) *Attorney, Agent, or Firm* — Joyce von Natzmer; Agris & von Natzmer LLP (57) ABSTRACT

The invention relates to "solid state" chemiresistor sensors with electric control of the affinity of a chemosensitive material. The configurations of the present invention enable the fast regeneration of the sensor after analyte binding, which therefore increases selectivity. In one embodiment the chemiresistor sensor is implemented as a multi-electrode chemiresistor, comprising 4 electrodes for the separate measurement of the resistance of the chemosensitive material and the contact resistance, and 2 further electrodes to control the redox state of the chemosensitive sensor material, thereby facilitating fast and effective regeneration of the sensor.

17 Claims, 9 Drawing Sheets

(56) References Cited

OTHER PUBLICATIONS

Lange U et al: "Separated analysis of 1,7-11, bulk and contact resistance of conducting 13-16, polymers: Comparison of simultaneous two—21,22, and four-point measurements with impedance 24,25 measurements" in: Journal of Electroanalytical Chemistry and Interfacialelectro Chemistry, Elsevier, Amsterdam, NL, vol. 622, No. 2, Oct. 15, 2008, pp. 246-251.

Kruszka J et al: "Simultaneous in situ 1,7-11, conductivity and ESR measurements of 13-16, electroactive polymers in electrochemical 21,24,25 cell" in: Review of Scientific Instruments USA, vol. 62, No. 3, 1991-03, pp. 695-699.

Leventis N et al: "Characterization of a 'solid-state' microelectrochemical diode employing a poly(vinyl alcohol)/phosphoric acid solid-state electrolyte: rectification at junctions between W03 and polyaniline" in: Chemistry of Materials USA, vol. 2, No. 5, 1990-09, pp. 568-576.

Biallozor S et al: "Study on polypyrrole as an electrode material in neutral solutions" in: Corrosion Science Nov. 1, 1998 Elsevier LTD GB, vol. 40, No. 11, Nov. 1, 1998, pp. 1873-1881.

Ando M et al: "Optical ozone-sensing properties of poly(2-chloroaniline), poly(N-methylaniline) and polyaniline films" in: Sensors and Actuators B, Elsevier Sequoia S.A., Lausanne, CH, vol. 108, No. 1-2, Jul. 22, 2005, pp. 528-534.

\* cited by examiner

MULTI-ELECTRODE CHEMIRESISTOR

CROSS-REFERENCE TO RELATED APPLICATIONS

This is the U.S. national stage of International application PCT/EP2010/004406, filed Jul. 13, 2010 designating the United States and claiming priority to European application no. EP 09075311.2, filed Jul. 13, 2009.

The invention relates to "solid state" chemiresistor sensors with electric control of the affinity of a chemosensitive material. The configurations of the present invention enable the fast regeneration of the sensor after analyte binding, which therefore increases selectivity. In one embodiment the chemiresistor sensor is implemented as a multi-electrode chemiresistor, comprising at least 2, preferably 4, electrodes for the separate measurement of the resistance of the chemosensitive material and the contact resistance, and at least 1, preferably 2, further electrodes to control the redox state of the chemosensitive sensor material, thereby facilitating fast and effective regeneration of the sensor.

BACKGROUND OF THE INVENTION

Conductive polymers have been previously used in chemo- and biosensors (see Lange et al, Anal. Chim. Acta, 614, 2008). All conductive polymers exhibit and intrinsic affinity for redox-active compounds and many exhibit an affinity for acidic or basic gases and solvent vapours. In order to achieve a specific interaction with the analyte, polymers may be modified with receptors. Receptors that have been immobilised to polymers exhibit an important advantage compared to other receptors. The conductive polymer wire enables a collective response, which leads to a significant increase in signal. Swager et al (Acc. Chem. Res., 31, 1998) demonstrate that a conjugated polymer receptor for methylviologen exhibits a 65 times larger signal amplification in comparison to a monomer receptor.

The application of conductive polymers for chemical- and biosensors can be implemented using various methods of detection. A detailed discussion of these aspects can be found in Lange et al, Anal. Chim. Acta, 614, 2008.

The most commonly used technology for signal transduction for chemiresistor sensors based on conducting polymers is the measurement of conductivity. Examples of such applications can be found in the following patents: US 2004040841, JP 2003302363, US 2007114138, US 2007029195, US 2003148534, US 2004202856, U.S. Pat. No. 6,493,638, DE 102004047466, RU 2174677, U.S. Pat. No. 5,869,007, U.S. Pat. No. 5,337,018 and U.S. Pat. No. 5,882,497. This technology exhibits various advantages: 1) small disruptions along the polymer chain can change the conductivity of the whole chain. Therefore, an increased sensitivity can be obtained in comparison to electrochemical or optical methods of measurement. 2) The measurement set-up is relatively simple, although enables a precise and highly sensitive measurement. 3) Measurements of conductivity can be implemented using nano wires of conductive polymers. 4) Single chemiresistors can easily be combined into arrays. 5) With the help of RFID technology, such measurements can be carried out without wire connection. There are multiple possible configurations that can be applied to in order to measure the conductometric responses of such sensors. Some of them are summarised in FIG. 1.

Figure 1:
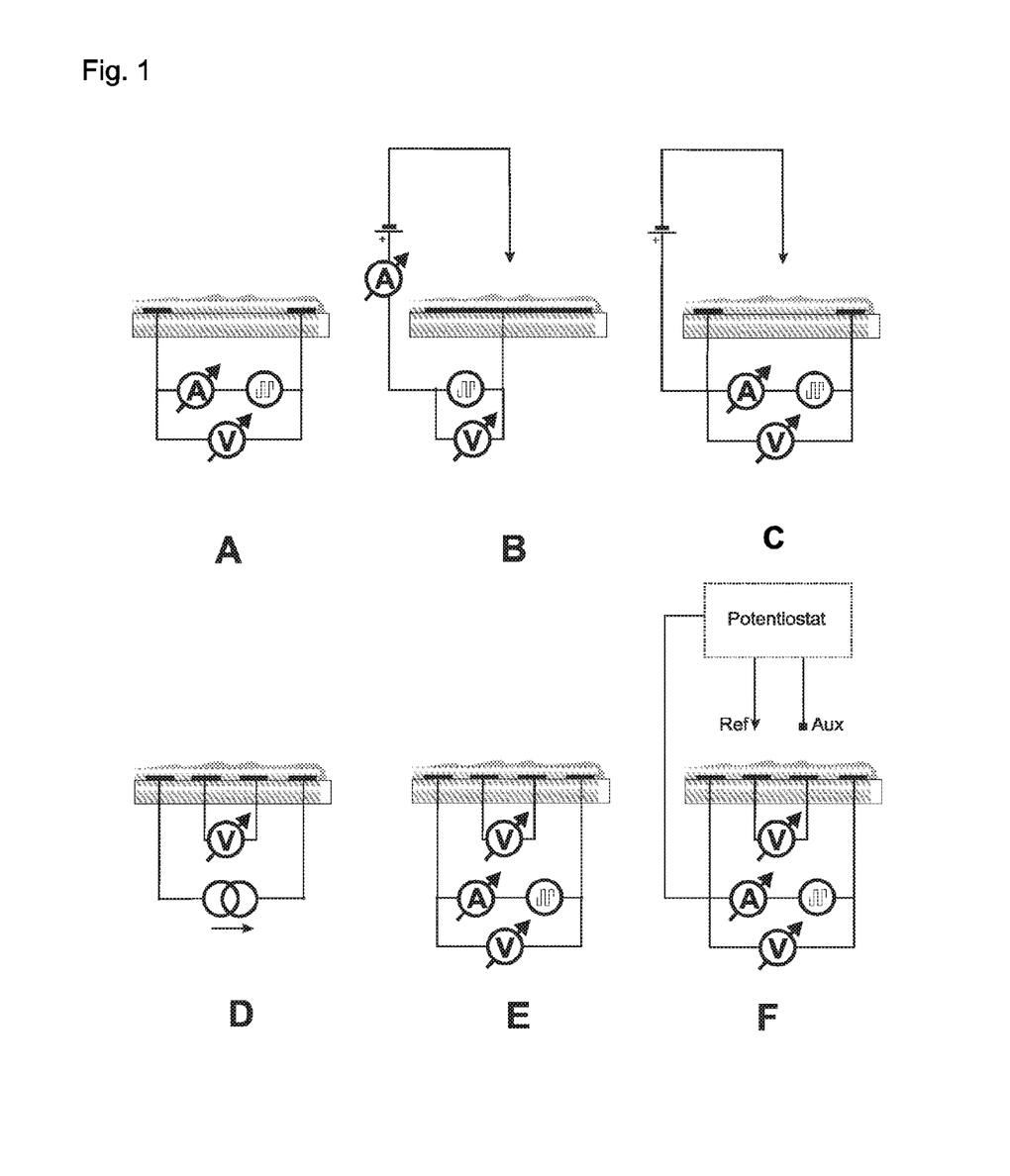
FIG. 1 Examples of configurations capable of measuring conductometric responses

In 2-point technology (FIG. 1$a$) the conductive material is applied to two electrodes that are separated by a narrow gap. The conductivity is then measured by the application of a constant current or voltage (dc or ac) between the electrodes and the resulting voltage or current is then measured. The more rarely used 4-point measurement technology measures the conductivity of the conductive layer without influence of the voltage drop between the conductive layer and the metal contacts (FIG. 1$d$). This technology has recently been modified so that the 2- and 4-point technologies have been combined (FIG. 1$e$).

A further possibility is the use of organic field transistors as sensors. Here the current is controlled between the source and the drain electrode by the gate voltage. Based on the similarity of the measurement configuration, Wrighton et al (J. Am. Chem. Soc., 1990) introduced the term electrochemical transistor for an apparatus based on a conductive polymer, in which the redox-state of the polymer is controlled by the voltage between the working electrode (source and drain) and a reference electrode (gate) (FIG. 1$c, f$). The measurements of electrical current between two or more electrodes on a substrate is the most practical method, however the low conductivity of the chemically sensitive films under conditions typical for bioanalytical measurements (neutral ph, low oxidation potential) can complicate these methods. In such cases measurement of the resistance between an electrode, which is modified with a chemically sensitive film, and another electrode in a solution, is often used (FIG. 1$b$). These measurements can be carried out using the commonly known 2- or 3-electrode configurations. One advantage of such measurements is that the ratio of electrode surface to film thickness is approximately 100 times greater, which leads to an approximately 100 times lower absolute resistance in comparison to the resistance of lateral measurements.

In most chemiresistors, changes in conductivity are measured using the 2-point technology. A low voltage direct current (approximately 5-100 mV) or a constant current is applied between the two electrodes, which are separated by a narrow gap, and the resulting current/voltage drop is measured. Such micro electrodes are most often produced with help of photolithography. Approximately 50-200 nm thick gold or platinum films are deposited onto oxidised silicon glass surfaces, using a very thin adhesive layer. The gap between the electrodes is normally between 1.5 μm and 100 μm, although smaller gaps are preferred due to the smaller amount of chemically sensitive material that must be used in order to cover the gap, which causes increased sensitivity. When the material is separated over the gap, larger gaps commonly lead to thicker polymer films and therefore to a loss of sensitivity. The pre-treatment of the electrode with for example hydrophobic silanes can enhance the growth of the polymer over the gap, whereby the pre-treatment of gold electrodes with thiol monomers enhances contact between the electrode and the polymer film and therefore reduces the influence of the contact resistance.

The application of a constant voltage or a constant current in order to measure changes in conductivity of sensors based on chemiresistors leads to various problems. Irreversible or slowly reversible changes in the film can occur, which can be avoided by the application of alternating current voltage or oppositely polarised direct current pulses. Additionally, a high voltage through a chemically sensitive film leads to heating of the film, which leads to the conductivity becoming sensitive to parameters such as air- or liquid flow. Another reason for maintaining the voltage as low as possible is the non-linearity of the current-voltage curve. However in contrast the signal to noise ratio increases with increasing voltage. Therefore a compromise must be found between a voltage that is high enough to produce an appropriate signal to noise ratio and the effect of heating.

Alternating current measurements have one advantage over direct current measurements. It has been reported that the noise during conductivity measurements exhibit a flicker noise behaviour and a decrease of 1/f (whereby f is the frequency) during increasing frequency. This noise behaviour was explained by a contribution of the contact resistance between single polymer grains on the total resistance of the polymer film. This intermediate grain resistance has a parallel switched capacity, which bridges the resistance at higher frequencies. Additionally, impedance analyses can be made for alternating current measurements, or simultaneous resistive and capacitive changes can be measured, which increases the sensor selectivity. A sensor that retrieves various frequencies has been reported. Measurements of a few selective frequencies are typically much faster than the measurement of impedance.

The use of multiple electrodes and the switching between electrodes enables an increase in the measurement through flow. Slater et al (Analyst, 118, 1993) used such multiple electrodes in order to create a multi layer gas sensor. Regarding measurement of electrical conductivity between electrodes at different distances, the authors proposed that it is possible to order or allocate the conductive zones of the polymers. Subsequently, the conductivity between electrodes positioned close together is most substantially influenced by a thin polymer layer which is close to the electrode substrate. Thin films were also found to be more sensitive to gases when compared to thick films.

The resistance measured by the 2-point technology includes the polymer resistance and the resistance between the contacts in the polymers. When the contact resistance is high, and in comparison with the polymer resistance shows only changes regarding the analytes, it can limit the sensitivity of the system. Most synthesis technologies for thin chemosensitive films lead to the creation of micrometer or submicrometer thick layers. Therefore the method from Cox and Strack (Solid-State Electron, 10, 1967), which is based on the change in the relationship between a contact area to the thickness of the material, can hardly be used in order to distinguish between the polymer and the contact resistances.

Importantly, this can be achieved through impedance spectroscopy, whereby broad frequency spectrums are measured, therefore enabling separation of the resistance of the polymer and the resistance between the polymer and the metal contacts. However, these measurements are relatively slow because a broad frequency band must be covered. Additionally, the results of the impedance spectroscopy are influenced by the selection of the electrical circuit for the data analysis. This problem can however be solved more easily using 4-electrode configuration-based measurement technologies.

In the 4-electrode configuration, the conductivity is measured by the application of constant voltage between two outer electrodes, whereby the difference in potential between two inner electrodes is measured. This difference in potential is measured using a voltmeter with high input resistance and is therefore not influenced by the drop in ohmic potential in response to the contact resistance of the inner electrodes. Four parallel metallic strips are commonly used as contacts for the 4-electrode configuration. For a more effective usage of the sensor surface when using the 4-point measurement, wound electrodes have been developed. Such electrodes have been used as single sensors and as arrays, comprising of 96 such electrodes, and enable a combinatorial investigation of material.

If the contact resistance is so high that it limits the dynamic range of the sensor signal, the application of a 4-electrode configuration of a higher sensitivity is required. On the other hand, 4-electrode measurements alone provide no information on the resistance of the contacts between film and metal. Many processes lead to the detachment or displacement of the film from the contacts or to the formation of poor conducting contacts. For example the common process of chemical immobilization of proteins has been reported to lead to a detachment of the polymer. On the other hand, the contact resistance can contain additional analytical information which can be useful for analysis.

The simultaneous 2- and 4-point resistance measurement (S24) provides a possibility to measure the 4- in addition to the 2-point resistance, whereby the subtraction of both values leads to the determination of the contact resistance. The relationship of the resistances, which are measured through the 2- and 4-point technologies, provides valuable information regarding the quality of the contact between middle and conductive film. The calculation of quantitative values from such measurements is based on the following idea. The 2-point technology provides the $R_2$ value, which is the sum of the film resistance in the two contact resistances, whereby the 4-point technology measures the film resistance $R_4$ between the middle points of the inner electrodes.

The contact resistance can therefore be calculated by $R_c = R_2 - \alpha \cdot R_4$, whereby $\alpha$ is the geometric factor. When the electrode geometry is the same for all examined polymers, the constant $\alpha$ can be used in order to calculate the contact resistance from the values $R_2$ and $R_4$. It has been demonstrated that small variations in $\alpha$ do not lead to qualitative changes in the behaviour of the contact resistance. This approach has been used to study the dependence of contact resistance between polypyrol and gold electrodes under various electrode potentials. These results have been compared with the results from impedance-spectroscopy. A strong agreement has been observed for a change of 4 orders of magnitude.

A number of other methods for quantitative estimation of the contact resistance have been described. This value can be obtained, for example, by switching between 4- and 3-electrode configurations. Measurements of the electric potential between the source and sense electrodes and the straight-line extrapolation of the drop in voltage allow one to calculate the voltage drop at the source and drain contacts. An examination of the resistance' dependence on the distance between two electrodes and the calculation of the contact resistance through the following extrapolation of this dependence has also been reported.

Monitoring of contact resistance or the ratio of the two- and four-point resistances allows us to make internal control of the sensor integrity: a desorption of sensor molecules from the electrode can be detected and thus distinguished from increase of the resistance of chemosensitive material.

One disadvantage of these methods of measurement is that they do not allow controt of the redox-state of the polymer or of any other chemosensitive material. This can however be carried out electrically through the fixing of the potential of the chemosensitive material in relation to a reference electrode. Such measurements are often designated as in-situ resistance measurements and the measurement configurations are commonly named electro-chemical transistors. This naming has been accepted in the literature and is therefore used herein. However such terms should not be confused with semi-conductors or organic transistors, which function in a different manner.

The first application of electrochemical transistors was described by White et al. in 1984. They use a symmetrical configuration, comprising three gold electrodes of three micrometers that were separated by a 1.4 micrometer-wide gap. The central electrode which was used to control the redox-state of the polymer was bound as a working-electrode with a potentiostat. Auxiliary- and reference electrodes were immersed in solution. Due to the similarity to field effect transistors the central gold microelectrode was designated "gate" and the two other electrodes designated "source" and "drain". This configuration has been further simplified by leaving out central electrode, whereby the control of the redox-state of the film is carried out by through the source or drain electrode. This allows an even smaller gap between the source and the drain electrode and therefore a faster reaction time. However with highly specific polymer resistance this asymmetric configuration can lead to variation or deviation in the condition of the polymer close to the second electrode and therefore to heterogeneous polymer properties between the source and drain electrodes.

A further simplification of the configuration of the electro-chemical transistor can be carried out by the replacement of the potentiostat with a reference electrode and serially connected potential source. However in this case the ohmic voltage drop at a low polymer resistance can lead to deviation from the applied potential. A difference in potential between the source and drain electrodes can be achieved by the application of a bipotentiostat. In this case the potentials of the source and drain electrodes are simultaneously controlled and a constant small difference in potential is maintained. The current through the drain and source electrodes comprise of faraday units, which are induced by the redox-reaction of the polymer and an ohmic component produced through the difference in electric potential between the electrodes.

An alternative technology relates to the combination of common 2- or 4-electrode configurations for the measurement of resistance with a reference electrode or using a potentiostat. When a constant voltage between the source and the drain electrodes is applied the measured current contains not only the current between the 2 electrodes but also the current between the film and the auxiliary or the reference electrode in the electrolyte. In order to solve this problem, voltage pulses with opposite polarity and low frequency (<1 Hz) or a triangular voltage pulse can be used. In such cases various methods are used in order to calculate the polymer resistance. Wrighton and colleagues calculate the increase in the I-V-curve at zero voltage (Paul et al. J. Phys. Chem. 89, 1441, 1985). When pulses instead of triangular wave forms are used, the voltage is usually measured at the end of each pulse, when transistent effects are minimal. In Kruszka et al (Rev. Sci. Instrum. 62, 695, 1991) the voltage from three consecutive measurements was calculated, whereby the current of the negative pulse was subtracted from the average current of the two positive pulses. The averaging of the positive and negative pulses provides almost the same results. The removal of current that traverses the electro-chemical cell is especially important when the current between the source and drain is very small.

In order to apply such electro-chemical transistors in sensor applications the factors which influence the in-situ-resistance should be considered. Such in-situ-measurements of resistance are commonly used to study thin conductive polymer films. This technology is often coupled to other technologies such as cyclic voltammetry, ESR or quartz crystal micro balance. However in most studies the 2-point resistance measurement is applied. The application of simultaneous 2- and 4-point measurements demonstrates that the data which is obtained through the 2-electrode configuration may contain significant mistakes regarding the contact resistance, especially regarding high polymer conductivity.

A modification of chemosensitive materials with enzymes, which directly interact with the material or release substances during the enzymatic cycle that influences the material resistance, represents a simple possibility for producing conductometric enzymatic biosensors. External references and auxiliary electrodes can be used in the simplest constructions (FIG. 1c), however these electrodes can not be directly applied to the microchip surface.

Solid state electro-chemical transistors were first reported by Chao (J. Am. Chem. Soc. 109, 6627, 1987). Such transistors exhibit a solid electrolyte which is precipitated over an array, which comprises of 8 microelectrodes. Two of these electrodes were used as counter electrodes, whereby the other 6 were bound to a conductive polymer film. A drop of silver adhesive was used as the reference electrode. The chip was covered with polyvinyl alcohol and used as a humidity sensor.

The influence of faradaic and non-faradaic processes on the gate electrode in regards to the performance of the electrode chemical transistors has been examined. The charge, which is necessary for the oxidation (doping) of the conductive polymer can be compensated for by the discharge of the double-layer of the gate electrode (non-faradaic process) or by a reduction process on the gate electrode (faradaic process). However the relatively small capacity of the ionic double-layer can limit the charge of the polymer oxidation. Faradaic processes have a much higher pseudo-capacity, which leads to a higher sensitivity of the transistor voltage in response to changes in the gate potential. In order to enable faradaic processes of the gate electrode, the gate electrode can be covered with a redox-active material. A large surface relationship between the gate and the work-electrode reduces the switching time.

The switching time and the charge of the transistor depend strongly on the amount of the polymer, which is necessary to bridge the gap between the source and the train electrode. A switching point of 0.1 milliseconds has been reported for PANI when using a gap of 50-100 nm. This construction was switched under the electrical charge of 1 nC. For a similar construction with 1.5 micrometer wide gap, approximately 100 times higher charge was required. Constructions with very small gaps are also used in sensors. The modification of polyanaline with glucose oxidise has been produced for in vivo applications as a biosensor for glucose.

Electrochemical transistors are produced from conductive polymers on flexible substrates. In this case PEDOT/PSS is used as a contact, channel and gate material. Fast switching times at low air humidity could be achieved, whereby a very hygroscopic solid electrolyte was used, which comprises of PSS, ethylene glycol, sorbitol and $LiClO_4$. There were various measurement configurations for such transistors proposed. The most simple is a 3 electrode electrochemical transistor. A solid electrolyte covers the channel between the source and outlet electrodes and the gate electrode. In modification of this configuration can be achieved when references are attached to a second gate electrode, which is in contact with the channel. This is a configuration similar to others whereby a central electrode is positioned as a gate electrode between the source and drain electrodes. This transistor was tested as a humidity sensor. The changes in conductivity of the channel at the gate voltage of 1.2 V depended strongly on the humidity-dependent conductivity of the solid electrolyte. In another configuration both gate electrodes are not in contact with the channel.

There are various problems with affinity sensors which are based on conductive polymers or other chemiresistive materials. Firstly, desorption of an analyte can be very slow. In order to accelerate this process the sensor can be heated (see e.g. DE 102004047466). However this can lead to damages of the chemosensitive material and it is time intensive to bring the sensor to the correct working temperature. The electric control of the affinity allows a different solution to this problem. Many chemosensitive materials (for example polyaniline, polypyrrol and their derivatives) demonstrate similar responses to changes in their protonation states and oxidation states which complicates the application of these materials as pH sensors. The electric control of the chemosensitive materials enables controlling the oxidation state.

Distinguishing between contact and film resistance of the polymer or any other chemosensitive material requires the application of the 4-point configuration for the resistance measurement, whereby additionally one reference or two reference electrodes can be applied in order for the redox state of the sensor material to be controlled. This approach has not been described in any prior art in regards to chemo resistors based on organic or inorganic conductive polymers.

A further aspect of the invention relates to the application of conductive polymers as optical signal transformers (e.g. US 2003148534, JP 4190142, JP 60202334, DE 10254841, G01N31/00, G01N21/55, G01N21/77, G01N31/22, G01N31/00, G01N21/55, G01N21/77, G01N21/77, G01N27/12). A typical optical detection method is based on changes in the absorption spectrum in the range between ultra violet and near infrared; however in some cases fluorescent or refractometry based detections methods could be applied (surface plasmon resonance). Also in these cases a regeneration of the highly sensitive sensor, through flushing with either gas or solution without analyte, is very slow and the chemical properties of the chemosensitive material could be modified via spontaneous oxidation or reduction during storage before application.

SUMMARY OF THE INVENTION

It was an objective of the invention to provide a chemiresistor sensor which overcomes the problems known in the prior art.

Surprisingly the invention solves the underlying problem by providing a Device for the measurement of optical or electrical properties of a chemosensitive material, comprising an isolated substrate onto which
 a. at least two work-electrodes,
 b. at least one reference-electrode, and
 c. at least one redox-active chemosensitive material
are mounted, whereby the work-electrodes are contacted with the chemosensitive material and the reference-electrode is contacted to the chemosensitive material over a conductive phase. All the electrodes are fixed on insulating or coated by insulating layer solid support.

In a preferred embodiment the present invention relates to a combination of the 4-point configuration, for the simultaneous measurement of the polymer conductivity and contact resistance, with the configuration of an electro-chemical transistor in order to control the redox-state of the chemosensitive material. This combination leads to the 6-point configuration, relating to a device for the measurement of optical or electrical properties of a chemosensitive material according to the present invention, comprising an isolated substrate onto which
 a. four work-electrodes,
 b. one reference-electrode and one auxiliary-electrode, and
 c. at least one redox-active chemosensitive material
are mounted, whereby the work-electrodes are contacted with the chemosensitive material and the reference- and auxiliary- electrodes are contacted to the chemosensitive material over a conductive phase.

In a preferred embodiment of the present invention the device as described herein is characterised in that at least one electrode, preferably the reference- and/or auxiliary-electrode, is capable of measuring and/or regenerating the redox-state of the chemosensitive material.

In a further preferred embodiment the regeneration of the chemosensitive material can be achieved via application of an electric potential.

In one embodiment of the present invention the format relates to a solid state chemosensor. The 4 central electrodes are intended for measurement of resistance, whereby the other two electrodes are used as auxiliary and reference electrodes.

In a preferred embodiment, the work-electrode, reference- and auxiliary-electrodes are connected to and capable of being controlled by a potentiostat. The potentiostat functions preferably by maintaining the potential of the working electrode at a constant level with respect to the reference electrode by adjusting the current at an auxiliary electrode. It preferably consists of an electric circuit which is usually described in terms of simple operational amplifiers.

The device can also be described as a chemosensor or chemoreceptor, which preferably transduces a chemical signal into an electrical signal. This is preferably used to detect certain chemical compounds in any given environment.

The device can be used for the measurement of the resistance of the chemosensitive material and/or for the measurement of the contact resistance of the chemosensitive material and electrode, whereby one of the electrodes serves as a work electrode.

In a preferred embodiment the device according to the present invention can be used as a sensor for the detection and/or measurement of one or more analytes, preferably redox-active substances, in solution or in gas.

In another preferred embodiment, the device can be used as a pH-sensor to determine the pH level of gases or liquid samples. In addition, the device can be used for the measurement of redox-active substances in solutions and in gases, whereby regeneration of the chemosensitive material is carried out via application of an electric potential which recovers the initial redox state of the chemosensitive material by oxidation or reduction of the chemosensitive material. This electrically-driven desorption of analyte can be considered as electrical control of the sensor affinity and of the redox-state of the sensor material.

A further aspect of the invention relates to the use of at least one electrode for the measurement and/or regeneration of the redox-state of a chemosensitive material, whereby the electrode and the chemosensitive material are mounted onto an isolated substrate. In a preferred embodiment the chemosensitive material is a conductive polymer. In a further preferred embodiment of the use of at least one electrode for the measurement and/or regeneration of the redox-state of a chemosensitive material, the electrodes functions as a work-electrode.

The invention further relates to a method for regenerating the redox-state of a chemosensitive material, preferably of a device of the present invention, characterised by the application of an electric potential over an electrode, preferably over reference- and/or auxiliary-electrodes.

The invention also describes a system, comprising at least two devices according to the present invention, whereby the devices are arranged on 1 or more substrates, whereby 2 to 10,000 substrates, preferably from 3 to 100 substrates, can be bound together. The configuration disclosed herein can be used as a chemical sensor in either small or large sensor arrays. In such a case, every sensor group, which comprises of 4 electrodes, should exhibit their own reference and auxiliary electrodes. When the sensor materials are not so different from one another and are either regenerated or controlled at the same value of electric potential, multiple sensor groups in a large configuration with a single reference or auxiliary electrode could be combined.

In a preferred embodiment the system comprises of multiple arrangements of 4-point measurements (n) and one or more reference-electrodes (m), whereby m≤n.

In another preferred embodiment the system comprises of multiple arrangements for 4-point measurement (n), one or more reference-electrodes (m) and one or more auxiliary-electrodes (k), whereby m≤n and k≤n.

The invention further describes a method for regenerating a redox-state of a chemosensitive material, comprising an isolated base onto which at least two work-electrodes and one reference-electrode or at least two work-electrodes, one reference- and auxiliary-electrode and at least one redox-active chemosensitive material, are mounted, whereby the work-electrodes are contacted with the chemosensitive material and whereby the reference- and/or auxiliary-electrode are contacted to the chemosensitive material over a conductive phase, whereby the redox-state of the chemosensitive material is measured and controlled by at least one electrode.

Another aspect of the present invention relates to a chemiresistor sensor for the detection and/or measurement of one or more analytes, preferably redox-active substances, in solution or in gas, comprising the device as described herein. In a preferred embodiment, the chemiresistor sensor is capable of measuring the resistance of the chemosensitive material and/or for the measurement of the contact resistance of the chemosensitive material and electrode.

One significant disadvantage of the chemiresistor sensors disclosed in the prior art is their limited ability to effectively regenerate the sensor chemosensitive material. It is common in the prior art that multiple sensors must be applied in order to make multiple measurements over a short period of time. The sensors are subsequently slowly regenerated, thus limiting the time interval between measurements, or simply discarded. The device and sensors of the present invention overcome these disadvantages, by providing a device that can be regenerated immediately and effectively, thus allowing repeated usage and measurement of analyte presence or concentration within very short time frames.

The chemosensor of the present invention exhibits unexpected advantages in light of the prior art. It was surprising that the regeneration of the chemosensitive material was so efficiently and quickly carried out by application of the electrode configuration and structure according to the present invention. The excellent regeneration of the chemosensitive material enables the rapid repetition of analyte measurement or detection with extremely high accuracy. This capability opens up new fields regarding the kinds of analytes and environments than can be tested with the device of the present invention. Considering the regeneration of the device is so fast and efficient, multiple measurements could be carried out in dynamic environments, such as rapidly moving air or liquid, therefore enabling a more precise measurement of the environment of interest.

DETAILED DESCRIPTION OF THE INVENTION

It is preferred that the conductive phase is a solid electrolyte or a liquid electrolyte with high viscosity. Solid electrolytes are materials that act as solid state ion conductors. Preferred solid electrolytes are beta-alumina solid electrolyte, beta-lead fluoride, zirconium dioxide, silver iodide, copper iodide, rubidium silver iodide, perovskite ceramics (such as strontium titanate, strontium stannate), or organic materials, chosen from the group comprising gels (polyacrylamide, agar), polyelectrolytes or ionomers. The advantage of the preferred electrolytes is that they are high conductors, which have a long durability. Furthermore, the costs for the production of the device are reduced by usage of the preferred electrolytes.

The chemosensitive material is preferably a conductive polymer. A conductive polymer is preferably an organic polymer that conducts electricity. Such compounds can be true metallic conductors or semiconductors. The advantage of conductive polymers is their processibility. Conductive polymers are also plastics and therefore can combine the mechanical properties (flexibility, toughness, malleability, elasticity, etc.) of plastics with high electrical conductivities. Their properties can be fine-tuned using the methods of organic synthesis. The chemosensitive material is preferably chosen from a group comprising polypyrrolle, polyaniline, polythiophen, polyindiol, PEDOT, polyporphirin, polythiazine, polyporfirine, graphene, carbon nanotube or chemical derivatives of any of these materials. It is also preferred that a layer of redox-active substance, preferably a conductive polymer, is arranged between the auxiliary-electrode and conductive phase.

Also encompassed by the present invention are various other redox-active chemoresistive materials such as non-polymerized redox-materials, non-polymerized redox-active materials in unredox-active polymer compositions, the fullerens, nanotubes, graphin, metallic or plastic nanoparticles or chemosensitive and redox-active colouring agents.

It is preferred that a chemical group with a strong affinity for the analyte, is covalently or physically bound to the chemosensitive material. The analyte can be any chemical, biological and biochemical gaseous or liquid sample. The analyte can be for example DNA, antibodies, prions, bacteria, viruses and any other object and/or object fragment or molecule which is relevant in biosciences, biochemistry and biotechnology. The invention is therefore not limited to specific applications and specific variables to be measured.

It was surprising that the device is suitable to detect gas or solution components in extremely low concentrations. Thus, it can be preferred, that the chemosensitive material has functional groups, such as polyaniline. This chemosensitive material has a surprising high affinity for acidic or basic gases, such as hydrogen chloride among others. The sensor allows the determination of gases in the ppb range without exhibiting significant cross-sensitivity to water vapour or carbon dioxide. It is furthermore characterized by a long-term stability at least for months. Functional groups can be e.g. amines or carboxylic acids. It was very surprising that a silver-coating, which is preferably used to cover the reference electrode, remarkably increases the sensitivity of the electrode. It also improves the durability and the response characteristics of the electrode and subsequently of the device. However, it is also preferred that a silver/silver-halogenid-layer covers the reference electrode, whereby the conductive phase comprises the corresponding halogenid-ion.

It is preferred that the electrodes are applied by a photolithography to a glass wafer. However, every solid electric isolating or conductive material that is covered with an isolation coat can surprisingly be used. The thickness of the electrodes is preferably 150 nm gold applied onto a preferably 15 nm adhesive layer of for example titan/wolfram. Various types of electrode geometry (for example folded or linear central electrodes) can be used.

In a preferred embodiment the device of the present invention is characterised in that a silver-coating is used to cover the reference electrode. In a further preferred embodiment the device of the present invention is characterised in that a silver/silver-halogenid-layer covers the reference electrode and the conductive phase comprises the corresponding halogenid-ion. In a further preferred embodiment the device of the present invention is characterised in that a layer of redox-active substance, preferably a conductive polymer, is arranged between the auxiliary-electrode and conductive phase.

The present invention exhibits various advantages over the state of the art. The device combines the advantages of both the 4-point configuration for measurement of resistance, with the electro-chemical transistors and the solid body sensors. No external electrodes are required for the measurement, which makes the device very affordable and furthermore allows further miniaturization of such a device.

It is preferred that at least one electrode, preferably two electrodes, measures and/or regenerates the redox-state of the chemosensitive material. The term redoxstate comes from the two concepts of reduction and oxidation and describes a chemical reaction in which atoms have their oxidation number or oxidation state changed. The term oxidation describes a loss of electrons, whereby the process reduction stands for the gain of electrons. It was surprising, that the redox-state of the chemosensitive material can be determined by an electrode, whereby the electrode is preferably a reference- or auxiliary-electrode. This allows for a quick and reliable determination of the redox-state of the material, without the need of further equipment. Furthermore, after the determination of the redox-state, the electrode can regenerate the chemosensitive material, which makes the constant usage of the chemosensitive material possible. The operating expenses are also reduced, as no exchange of the chemosensitive material is necessary. The regeneration of the chemosensitive material also increases the measuring accuracy, by increasing the sensitivity and reducing the measurement errors.

The regeneration is conducted by application of corresponding potential to the chemosensitive layer through controlling electrode(s) (i.e. auxiliary and/or reference electrode). This potential shift is in anodic direction if an interaction with analyte leads to the reduction of chemosensitive material or to cathodic direction if the interaction with analyte leads to the oxidation of chemosensitive material. The potential application duration depends on particular system and is typically in the seconds- or tens of the seconds time scale.

In another preferred embodiment, the detector component of the device is an optical device, especially a spectrophotometer or a spectrofluorometer. Another advantage of the invention is the electric control of the redox-state of the chemosensitive material and the preferred detection by optical spectroscopy. The detection is carried out either through reflection or transmission spectroscopy. The same configurations are also used for fluorescence detection. This allows the reliable and quick detection of for example a gas by the device.

It was surprising, that a redox-state of a chemosensitive material can be measured and regenerated also if the chemosensitive material is mounted onto an isolated gate layer. The chemosensitive material is preferably a conductive polymer. As isolated base materials like Si covered by $SiO_2$, $Al_2O_3$, glass or polymer foils can be used. The materials should be electrically isolating and chemically resistant towards the analyte and other substances of the analyte matrix.

The terminology of the present description is mainly directed towards conducting polymers. The terms conducting polymer or chemosensitive material or chemosensitive film also relate however to any other red-ox active chemosensitive materials, for example different not-polymerized redox active materials in the form of molecules, nanoparticles, adsorbed or immobilized layers, modified and non-modified graphenes, fulerenes, carbon nanotubes, red-ox active non-conjugated oligo- and polymers. Furthermore, one can combine red-ox active non-chemosensitive compounds with chemosensitive compounds; this may be prepared as a mixture, adsorbed or immobilized layer or as defined chemical groups conjugated with redoxactive materials.

FIGURES

The following figures and examples demonstrate the effect of the invention:

FIG. 1: Main configuration for the measurement of the resistance of thin chemosensitive conductive films. A: 2-point configuration without fixing of the polymer potential. B: Typical configuration for the electro-chemical experiment. C: 2-point configuration with fixing of the polymer potential. D: Classical 4-point technology. E: S24 configuration, which allows the simultaneous 2- and 4-point measurement without fixation of the polymer potential. F: S24 configuration with fixation of the electrode potential.

Figure 2:
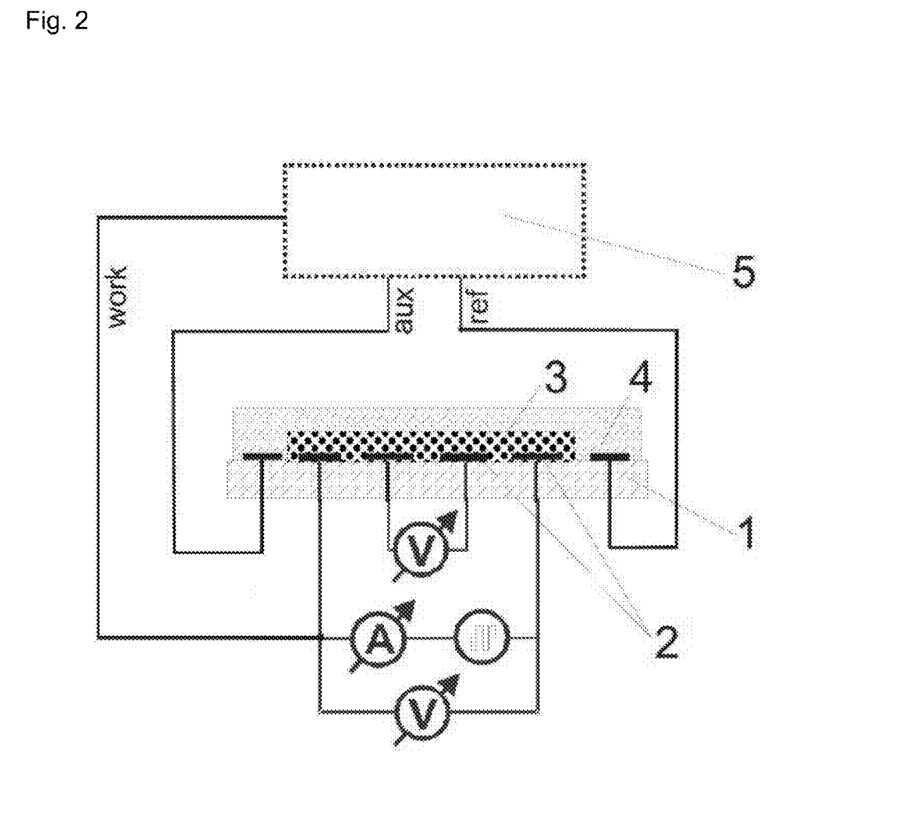
FIG. 2 A preferred embodiment of the present invention

FIG. 2: 6-electrode configuration for chemo resistors: 1—solid surface. 2—electrodes. 3—chemosensitive material (for example conductive polymer). 4—solid electrolyte (or gel electrolyte). 5—potentiostat. The 4 inner electrodes are used for the 4-point resistance measurement and enable the contact and film resistances to be separated. The two outer electrodes are reference and auxiliary electrodes. These electrodes enable the control of the redox-state of the sensor film.

Figure 3:
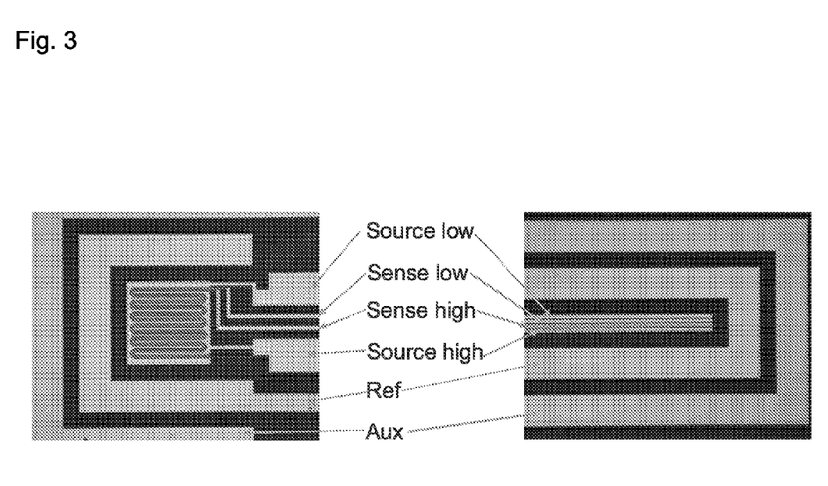
FIG. 3 A preferred configuration of electrodes for a 6-point measurement

FIG. 3: Electrodes for the 6-point measurement with folded (left) and linear (right) four-stripe work electrodes for the simultaneous 2- and 4-point measurement. The two outer stripes are used as reference and opposition electrodes.

Figure 4A:
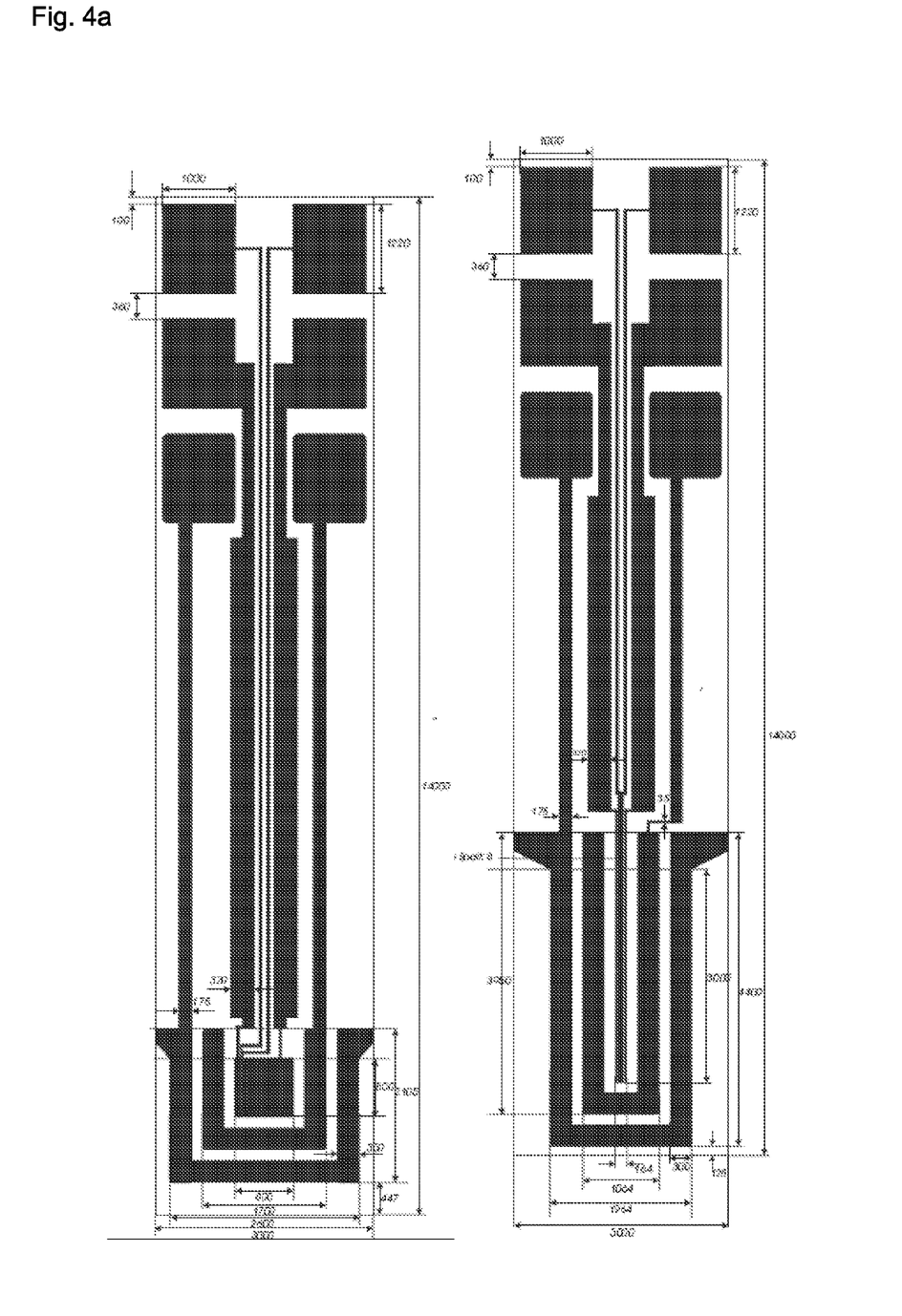
FIG. 4A/4B A preferred embodiment of electrodes for 6-point measurement
Figure 4B:
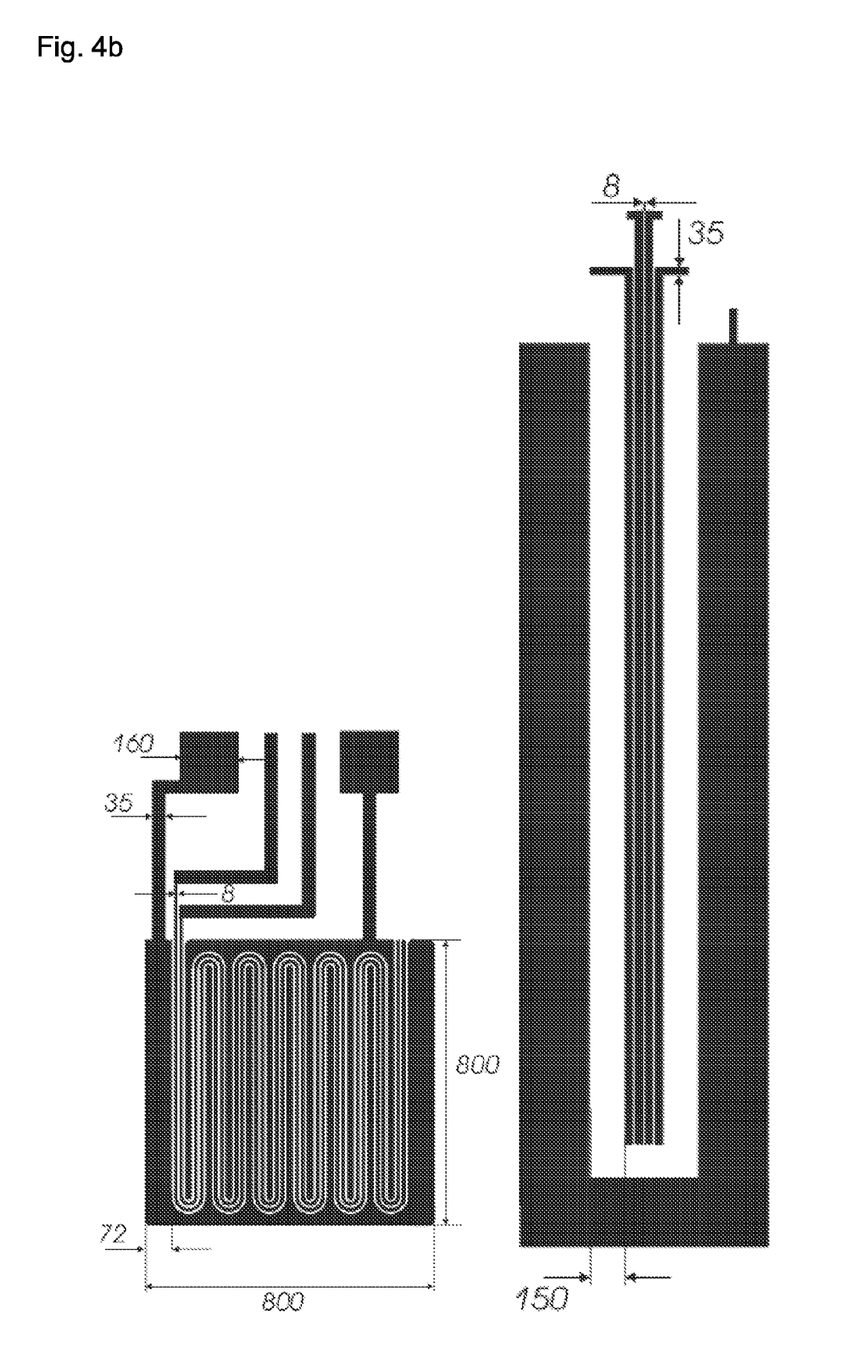

FIG. 4: A, B: Design of an electrode for the 6-point configuration (the active portion is demonstrated in the zoom section of FIG. 4).

Figure 5:
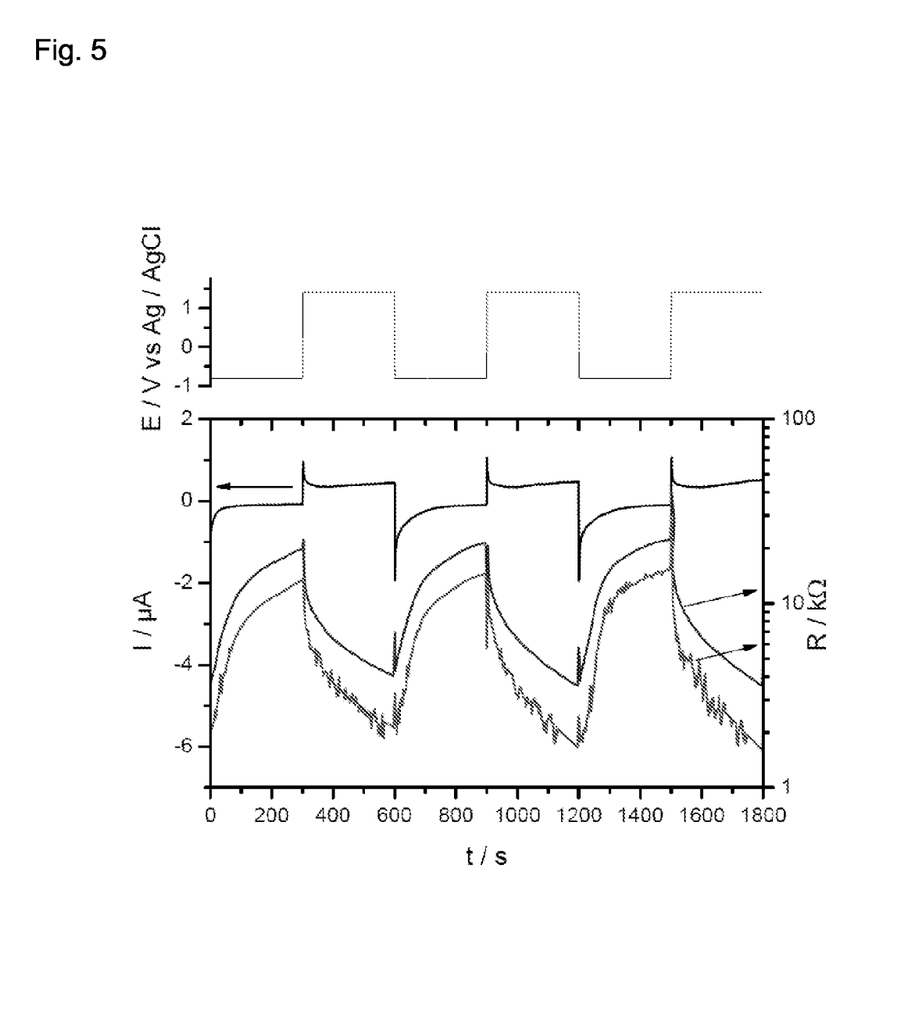
FIG. 5/6 Examples of measurements with one preferred embodiment of the invention FIG. 7 A preferred embodiment of an optical sensor FIG. 8 A preferred embodiment of a system with individual (above) or shared (below) reference or reference and auxiliary electrodes

FIG. 5: Testing the measurement configuration through the exposure of oxidation and reduction pulses with the simultaneous measurement of the resistance of the oxidation and reduction current shows that the potential between the reference and work electrodes can control the redox-state of the sensor.

Figure 6:
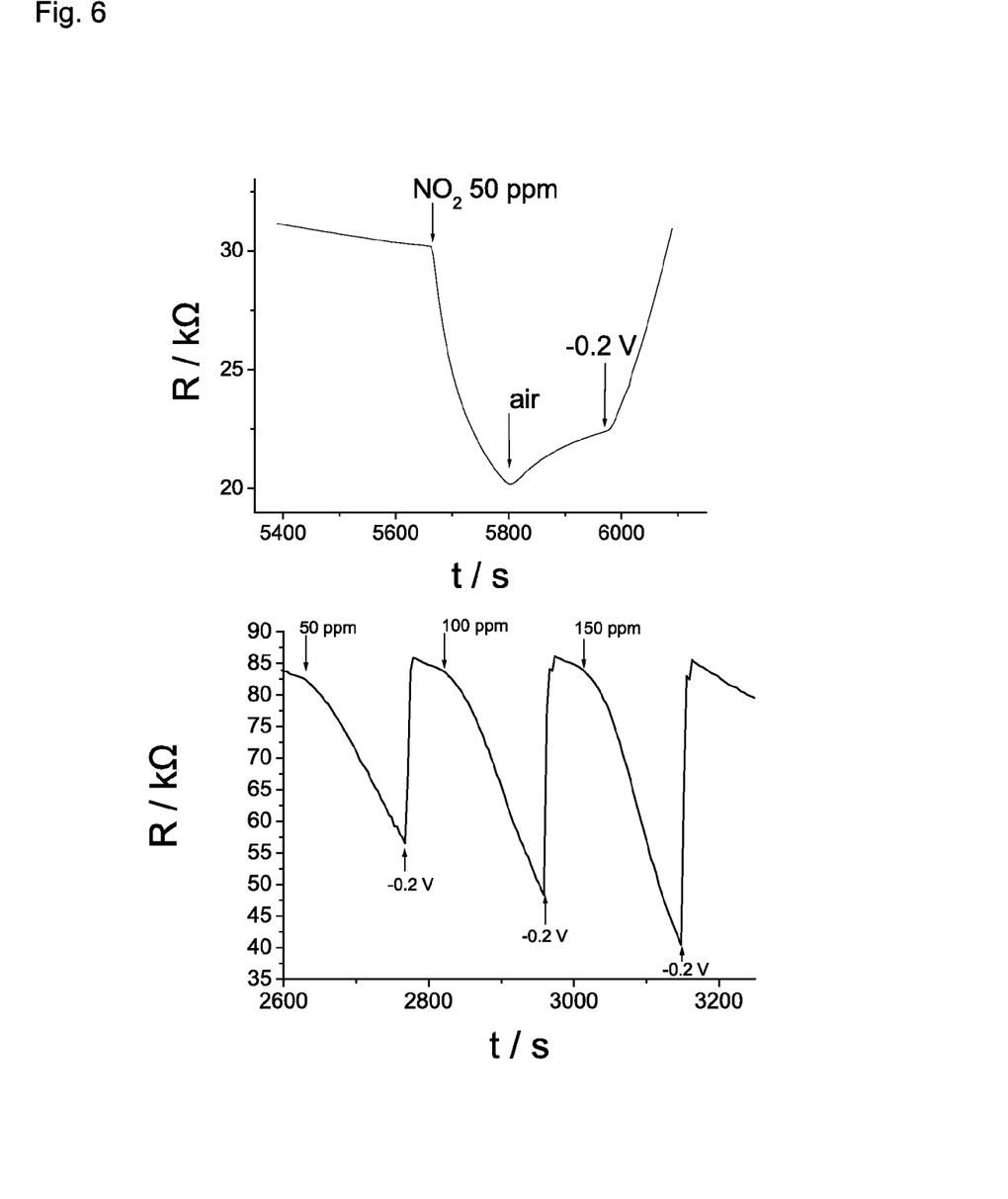

FIG. 6: The exposure of a Polythiophene modified chemo resistor to −150 ppm $NO_2$ leads to oxidation of the Polythiophenes and a reduction in the electrical resistance. The sensor regeneration in air is very slow, although a 100 sec pulse of a reduction potential (−200 mV) leads to the complete regeneration of the sensor. This process can be repeated multiple times.

Figure 7:
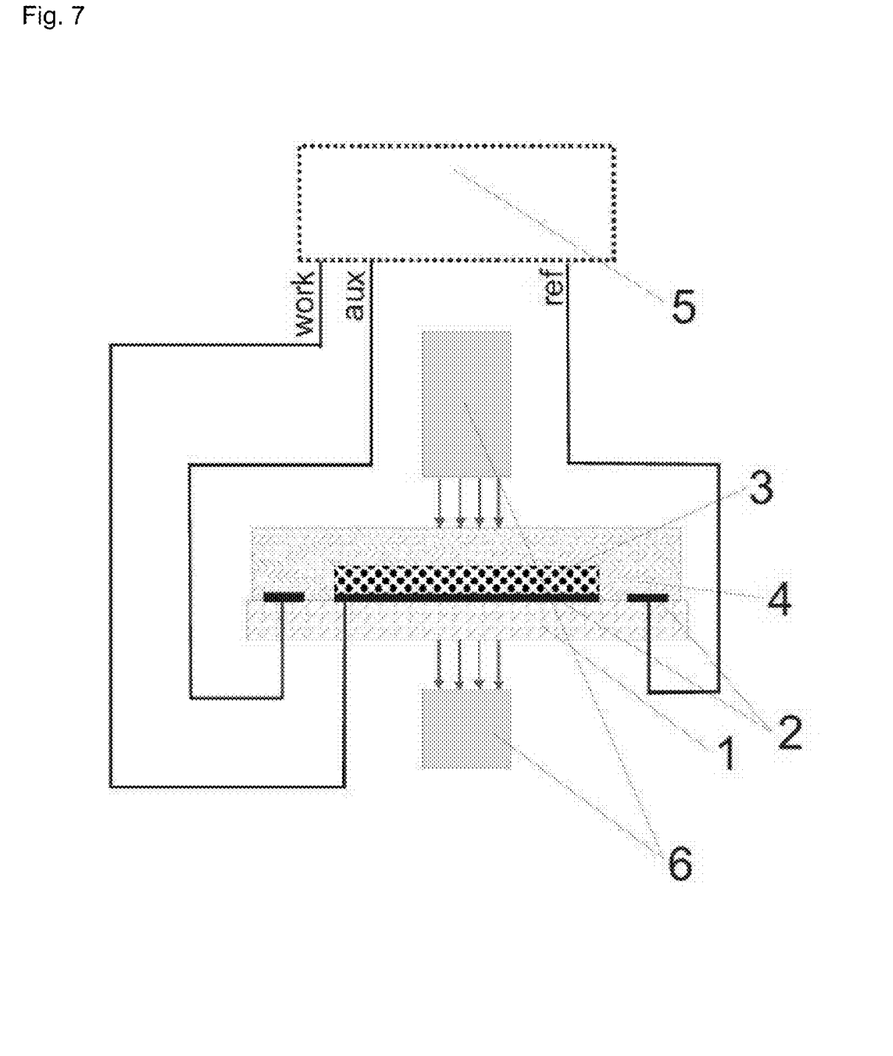

FIG. 7: Design of the optical sensor of the electro-chemical control of the redoxstate of the chemosensitive material. Special materials: 1—solid transparent support (glass). 2—electrode or conductive transparent glass cover (indium-tin-oxide). 3—chemosensitive material. 4—solid electrolyte (multilayer of Polystyren-Sulfate and Poly(allylamine hydrochlorid), produced via a layer-by-layer precipitation. 5—potentiostat. 6—spectrophotometer.

Figure 8:
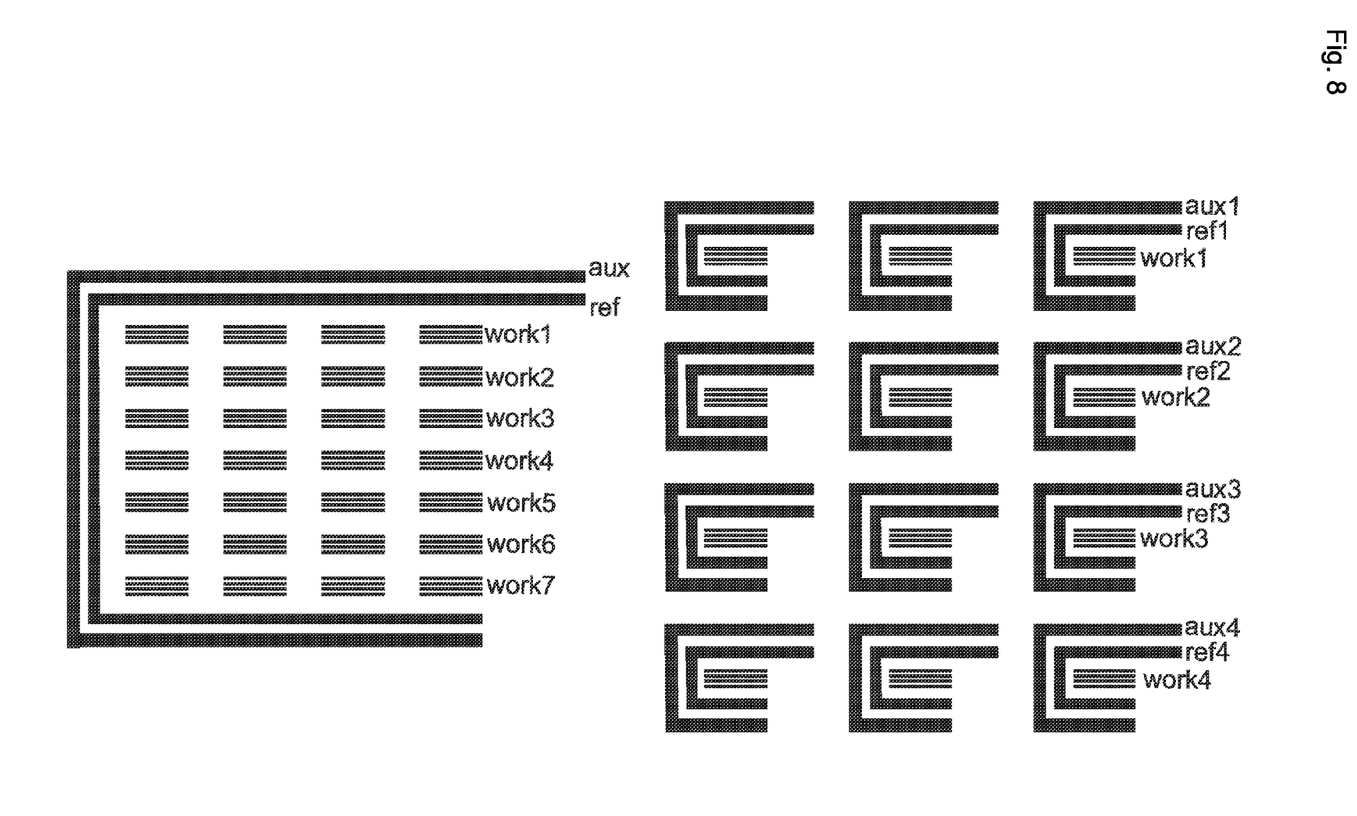

FIG. 8: A combination of the sensor formation in arrays with individual (above) or shared (below) reference or reference and auxiliary electrodes.

EXAMPLES

Example 1

Preparation of the Electrode and Testing

The electrodes presented in FIGS. 3 and 4 were used. The thickness of each electrode in this example was 150 nm of gold on a 15 nm adhesive layer of titan/wolfram applied on glass. This system (as described in Lange et al, J. Electroanal. Chem. 622, 246, 2008) was used in order to measure the 4- and 2-point resistance simultaneously and to calculate the contact and film resistances. A potentiostat "radiometer PGSTAT 201" was used in order to control the redox-state of the chemosensitive material.

The reference electrode was modified through electro-chemical reduction from silver (precipitation by −0.44 V vs $CuSO_4$ from a solution of 0.1 M $AgNO_3$ and 0.2 M EDTA which contains 1.5 M $NH_3$). The electrode is thereafter covered with silver chloride (oxidation of the silver in 0.1 M HCl at 1 V vs Ag/AgCl). The auxiliary electrode and the work electrode are electro-chemically modified with polythiophene (polymerization at 1.35 V vs $Ag/Ag^+$ from a 0.1 M solution of thiophen in 90% BFEE/10 acetonitrile). Finally, the sensor is covered with a solid electrolyte of polystyrenesulfonate and polyallylaminhydrochlorid (layer by layer precipitation from 0.1% solution of the polymer in water which contains 0.1 M NaCl, 5 layers). The test of the electrode through the application of oxidation and reduction pulses (FIG. 5) with the simultaneous measurement of the resistance and oxidation/reduction current demonstrates that the potential between the reference and work electrodes controls the redox-state of the sensor.

Example 2

Measurement of a Gas Analyte

The electrodes which were produced according to example 1 were used for the detection of highly diluted $NO_2$. The results of the measurement are demonstrated in FIG. 6. The exposure of a sensor to $NO_2$ containing air leads to an oxidation of the polythiophene into a dropping resistance. The spontaneous regeneration via flushing with air is very slow, whereby a short pulse with a cathodic voltage leads to the fast reduction of the chemosensitive material and leads to the regeneration of the sensor completely. The regeneration process can be carried out repeatedly (FIG. 6).

Example 3

Preparation of the Sensor for Spectroscopy

The electrodes which are described in example 1 are used for the reflection spectroscopy experiments. The potential is controlled through the potentiostat "radiometer PGSTAT 201". Changes in the optical spectrum after exposure to analytes are measured by the spectrophotometer with the assistance of fibre optics. The samples for the transmission spectroscopy are produced on the surface of indium-tin-oxide covered glass (FIG. 7). The indium-tin-oxide-layer is structured through the mechanical separation of the conductive layer. The measurement was carried out using a spectrophotometer.

For pH-measurements polyanilin or polypyrol is used as the sensitive layer. The measurements are carried out at constant potential.

One with ordinary skill in the art will recognize from the provided description, Figures and examples, that modifications and changes can be made to the various embodiments of the invention without departing from the scope of the invention defined by the following claims and their equivalents.

REFERENCE SYMBOL LIST 1 substrate
2 electrode
3 chemosensitive material
4 solid electrolyte
5 potentiostat
6 spectrophotometer

The invention claimed is:

1. A device for measuring optical or electrical properties of a chemosensitive material, comprising an isolated substrate onto which the following are mounted:
   a. at least one redox-active chemosensitive material,
   b. at least four work electrodes which are in contact with the redox-active chemosensitive material and which comprise at least two inner and two outer work electrodes, said inner work electrodes being positioned between the at least two outer work electrodes,
   c. at least one reference-electrode and at least one auxiliary-electrode,
   d. a conductive phase, and
   e. a voltmeter,
wherein:
   the two inner work electrodes are connected to the voltmeter,
   the at least one reference-electrode and the at least one auxiliary-electrode are in contact with the chemosensitive material via the conductive phase,
   the at least one reference-electrode and/or the at least one auxiliary-electrode are configured to measure and/or regenerate the redox-state of the chemosensitive material, and
   the device is a chemosensor.

2. The device according to claim 1, wherein the reference-electrode and the auxiliary-electrode, are configured to measure and/or regenerate the redox-state of the chemosensitive material.

3. The device according to claim 1, wherein the device is configured to apply an electric potential to the chemosensitive material to regenerate the same.

4. The device according to claim 1, further comprising an optical detector.

5. The device according to claim 1, wherein the conductive phase is a solid electrolyte.

6. The device according to claim 1, wherein the chemosensitive material contains a chemical group, which is covalently or physically bound to the chemosensitive material.

7. The device according to claim 1, wherein a silver-coating is used to cover the reference electrode.

8. The device according to claim 1, wherein a layer of redox-active substance, is arranged between the auxiliary-electrode and the conductive phase.

9. The device according to claim 1, wherein at least one electrode selected from the group consisting of the work-electrode, the reference-electrode and the auxiliary-electrode is connected to and capable of being controlled by a potentiostat.

10. The device according to claim 1 comprising at least two devices,
wherein the devices are arranged on one or more substrates, whereby from 2 to 10,000 substrates are bound together.

11. The device according to claim 10, comprising multiple arrangements of 4-point measurements (n) and one or more reference-electrodes (m), whereby m≤n.

12. The device according to claim 10, comprising multiple arrangements for 4-point measurement (n), one or more reference-electrodes (m) and one or more auxiliary-electrodes (k), whereby m≤n and k≤n.

13. A chemiresistor sensor for the detection and/or measurement of one or more analytes, in solution or in gas, comprising the device according claim 1.

14. The chemiresistor sensor according to claim 13, which is capable of measuring the resistance of the chemosensitive material and/or for the measurement of the contact resistance of the chemosensitive material and electrode.

15. The device according to claim 1,
wherein the reference-electrode is configured to measure and/or regenerate the redox-state of the chemosensitive material.

16. The device according to claim 5,
wherein the solid electrolyte is an organic material selected from the group consisting of gels, polyelectrolytes and ionomers.

17. A device for measuring optical or electrical properties of a chemosensitive material, comprising an isolated substrate onto which the following are mounted:
at least two work-electrodes,
at least one reference-electrode and at least one auxiliary-electrode, and
at least one redox-active chemosensitive material,
wherein:
the work-electrodes are in contact with the redox-active chemosensitive material and
the at least one reference-electrode and the at least one auxiliary-electrode are in contact with the chemosensitive material via a conductive phase,
the at least one reference-electrode and/or the at least one auxiliary-electrode are adapted to measure and/or regenerate the redox-state of the chemosensitive material,
the device is a chemosensor, and
a silver/silver-halogenid-layer covers the reference electrode and wherein the conductive phase comprises the corresponding halogenid-ion.

* * * * *